United States Patent
Thomas et al.

(10) Patent No.: US 6,666,095 B2
(45) Date of Patent: Dec. 23, 2003

(54) ULTRASONIC PIPE ASSESSMENT

(75) Inventors: Graham H. Thomas, Livermore, CA (US); Valerie L. Morrow, Livermore, CA (US); Harold Levie, Livermore, CA (US); Ronald J. Kane, Pleasanton, CA (US); Albert E. Brown, Hayward, CA (US)

(73) Assignee: The Regents of the University of California, Oakland, CA (US)

( * ) Notice: Subject to any disclaimer, the term of this patent is extended or adjusted under 35 U.S.C. 154(b) by 33 days.

(21) Appl. No.: 10/001,032

(22) Filed: Nov. 30, 2001

(65) Prior Publication Data

US 2003/0101821 A1 Jun. 5, 2003

(51) Int. Cl.[7] ............................................... G01N 29/04
(52) U.S. Cl. ......................................... 73/623; 73/592
(58) Field of Search .......................... 73/592, 623, 644, 73/622

(56) References Cited

U.S. PATENT DOCUMENTS

| 3,255,626 | A | * | 6/1966 | van der Veer ................ 73/644 |
| 4,403,510 | A | * | 9/1983 | deWalle et al. ............... 73/644 |
| 4,876,672 | A | * | 10/1989 | Petermann et al. ........... 73/623 |
| 5,001,932 | A | * | 3/1991 | Light et al. .................... 73/644 |
| 5,150,989 | A | | 9/1992 | Long, Jr. et al. |
| 5,359,898 | A | | 11/1994 | Latimer |
| 5,717,169 | A | * | 2/1998 | Liang et al. ................... 73/623 |
| 5,767,410 | A | | 6/1998 | Lareau et al. |
| 6,076,407 | A | * | 6/2000 | Levesque et al. ............. 73/623 |
| 6,079,273 | A | | 6/2000 | Latimer et al. |
| 6,148,672 | A | | 11/2000 | Cawley et al. |

FOREIGN PATENT DOCUMENTS

WO    WO 00/42425 A1    7/2000

* cited by examiner

Primary Examiner—John E. Chapman
(74) Attorney, Agent, or Firm—Eddie E. Scott; Alan H. Thompson

(57) ABSTRACT

An ultrasonic pipe or other structure assessment system includes an ultrasonic transducer positioned proximate the pipe or other structure. A fluid connection between the ultrasonic transducer and the pipe or other structure is produced. The ultrasonic transducer is moved relative to the pipe or other structure.

14 Claims, 2 Drawing Sheets

ULTRASONIC PIPE ASSESSMENT

The United States Government has rights in this invention pursuant to Contract No. W-7405-ENG-48 between the United States Department of Energy and the University of California for the operation of Lawrence Livermore National Laboratory.

BACKGROUND OF THE INVENTION

1. Field of Endeavor

The present invention relates to pipe or other structure assessment and more particularly to ultrasonic pipe or other structure assessment.

2. State of Technology

U.S. Pat. No. 5,150,989 provides the following information, "It is generally well known that conduits or pipes which are employed for conducting fluids, for example, sanitary sewer pipes, storm sewer pipes, water lines and gas lines, frequently require repair due to leakage. The leakage may be inwardly, from the environment into the pipe, or outwardly, from the pipe into the environment. Leakage of this type may be due to improper initial installation of the pipe, deterioration of the pipe itself due to aging or the effects of corrosive materials, cracking of the pipe or pipe joints due to environmental conditions such as earthquakes or similar natural or man-made vibrations, or any other such causes. Regardless of the cause, such leakage is undesirable, at best, and may result in waste of the fluid being carried by the pipe, damage to the environment and the possible creation of public health hazards. Because of ever increasing labor and machinery costs, it is becoming increasingly more difficult, at least economically, to dig up and replace those pipes or portions of pipes, which may be leaking. As a result, various methods have been devised for the in situ repair or rehabilitation of the existing pipes, thereby avoiding the expenses and hazards involved in digging up and replacing the pipes."

International Patent Application No. WO0042425 for a subsurface pipeline inspection probe by James Phillip Cull, published Jul. 20, 2000 provides the following information, "Traditionally, subsurface pipelines such as sewerlines and storm water drains have been inspected using manual access. This involves a person entering the pipeline system and carrying out a manual inspection of pipe walls. However, this method reveals only surface defects in the pipe walls and gives no information on defects in the surrounding soils. This method also has inherent dangers and health risks for the person carrying out the inspection. Remote controlled Closed Circuit Television (CCTV) has also been employed in inspecting subsurface pipelines. This method involves the use of a small camera which is mounted on the end of a long flexible cable. The camera is placed into the pipeline through an access opening and is then remotely controlled from the surface. This method removes the dangers involved in a person entering the pipeline, however, this method again reveals only surface defects in the pipe walls and gives no information on defects in the surrounding soils. In order to inspect the bedding of a subsurface pipeline and to detect defects in the surrounding soils, more elaborate techniques have been employed such as ground probing radar (GPR) and seismic methods."

U.S. Pat. No. 6,101,951 for a robot for the repair of sewer pipes by Alwin Sigel, patented Aug. 15, 2000 provides the following information, "The use of robots in the repair of sewer pipes which are not man-sized is already known. Such robots, which are provided with a drive means for moving them through sewer pipes, are suitable, e.g., for the cleaning of sewer pipes, for grinding off irregularities or protrusions or for the mending of leaks. A known multi-segment robot for the above purposes is provided with a rotary head carrying a plurality of treatment tools and a camera. By means of a rotary motor, the rotary head and the robot arm connected thereto can be rotated in a controlled manner by up to 500 degrees about the longitudinal axis. Behind the rotary motor, which is supported on the sewer pipe wall by support wheels, a switch and relay unit is arranged for controlling the functions of the motor. If, for instance, the robot is used to fill leaks or other gaps, a press-out container will be arranged behind the switch and relay unit. The material to be applied is pressed via a hose from the press-out container to the tool arranged on the rotary head and thus can be applied by the tool. Arranged behind the press-out container is a carriage unit for moving the multi-segment robot through the sewer pipe under treatment. For this purpose, the carriage, serving as a tractor, comprises a plurality of wheels driven by a traction motor."

U.S. Pat. No. 6,079,273 for EMAT inspection of header tube stubs by Paul J. Latimer, assigned to McDermott Technology, Inc. and The Babcock & Wilcox Company, patented Jun. 27, 2000, provides the following description, "A method for non-destructively testing closely-spaced objects, such as header tube stubs for a furnace or boiler using electromagnetic acoustic transducers (EMATs) having meander coil sensors. The small size of the sensor combined with the need to move the sensor only a small fraction of the circumference of a tube to scan the entire circumference of the tube under test permits easy and accurate testing of an entire tube, even when the tube is one of a closely-spaced bundle."

U.S. Pat. No. 5,359,898 for hydrogen damage confirmation with EMATs by Paul J. Latimer, assigned to The Babcock & Wilcox Company, patented Nov. 1, 1994, provides the following description, "A method and apparatus for use in confirming hydrogen damage in a boiler tube comprises a pair of electromagnetic acoustic transducer coils which are mounted for movement toward and away from each other. An electromagnet produces pulses that generate acoustic beams across a chord and within the wall thickness of the boiler tube. For adapting to boiler tubes of different outside diameters, the transducers coils are mounted on a resilient member so that the coils can be pressed against the outer surface of coils having a variety of outside diameters. The angle of the acoustic beam between the coils must also be adjusted, however, and this is done by changing the frequency of energy applied to the coils."

U.S. Pat. No. 6,148,672 for inspection of pipes by Peter Cawley et al, assigned to Imperial College of Science, Technology of Medicine, patented Nov. 21, 2000, provides the following description, "An apparatus and a method for inspecting elongate members, especially pipes, using Lamb waves. The apparatus and method provide for the propagation of an axi-symmetric Lamb wave of a single mode in one direction along the pipe. A receiver is provided to receive the Lamb wave after its passage along the pipe and convert the received wave for storage, processing and analysis to determine whether or not there are faults present in the pipe. The apparatus includes at least one and usually several excitation rings each having a plurality of Lamb wave exciters deployed in equiangular spacing in a ring clamping structure whereby each exciter can be pressed with equal force against the surface of the pipe under inspection."

U.S. Pat. No. 5,767,410 for Lamb wave sonar probe for crack detection and measurement in thin-walled tubing by John P. Lareau et al, assigned to Combustion Engineering, Inc., patented Jun. 16, 1998, provides the following description, "A probe inspects steam generator tubing for defects. The probe includes a transducer which generates a localized sonar Lamb wave. The sonar wave is transferred to the tubing by a coupling medium, such as water, that physically couples the transducer and the tubing. Defects in the tubing reflect the sonar wave to the probe which detects the reflections. The results are then used to determine the length and depth of such defects as cracks, pitting, and thinning. The localized sonar wave performs an inspection sensitive enough to detect ligaments between crack segments. This allows highly accurate predictions of tubing integrity and rupture strength."

SUMMARY OF THE INVENTION

Features and advantages of the present invention will become apparent from the following description. Applicants are providing this description, which includes drawings and examples of specific embodiments, to give a broad representation of the invention. Various changes and modifications within the spirit and scope of the invention will become apparent to those skilled in the art from this description and by practice of the invention. The scope of the invention is not intended to be limited to the particular forms disclosed and the invention covers all modifications, equivalents, and alternatives falling within the spirit and scope of the invention as defined by the claims.

A system for assessing pipe or other structure is provided by positioning an ultrasonic transducer proximate the pipe or other structure, producing a fluid connection between the ultrasonic transducer and the pipe or other structure, and moving the ultrasonic transducer relative to the pipe or other structure. In one embodiment of the invention, the system includes an ultrasonic transducer. The ultrasonic transducer is carried by a sensor arm and is moved proximate the pipe or other structure. A fluid connection between the ultrasonic transducer and the pipe or other structure is produced. In one embodiment a host pipe produces a column of fluid between the ultrasonic transducer and the pipe or other structure. In one embodiment the sensor arm is located inside the host pipe.

The invention is susceptible to modifications and alternative forms. Specific embodiments are shown by way of example. It is to be understood that the invention is not limited to the particular forms disclosed. The invention covers all modifications, equivalents, and alternatives falling within the spirit and scope of the invention as defined by the claims.

BRIEF DESCRIPTION OF THE DRAWINGS

The accompanying drawings, which are incorporated into and constitute a part of the specification, illustrate specific embodiments of the invention and, together with the general description of the invention given above, and the detailed description of the specific embodiments, serve to explain the principles of the invention.

DETAILED DESCRIPTION OF THE INVENTION

Figure 1:
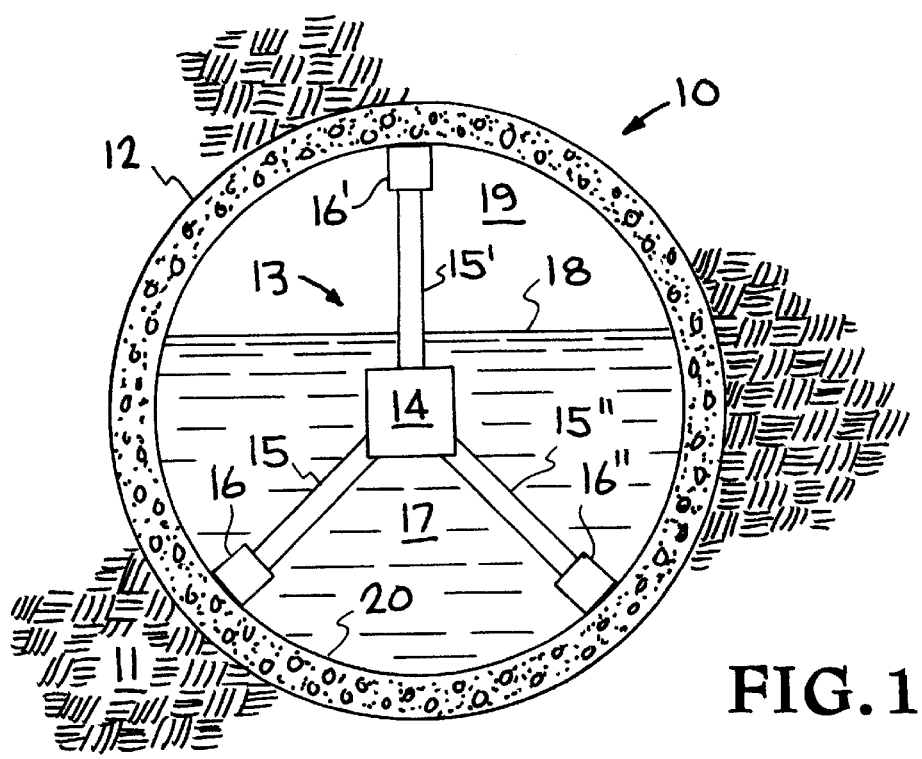
FIG. 1 illustrates an embodiment of a pipe or other structure assessment probe system constructed in accordance with the present invention.

Referring now to the drawings, to the following detailed information, and to incorporated materials; a detailed description of the invention, including specific embodiments, is presented. The detailed description serves to explain the principles of the invention. The invention is susceptible modifications and alternative forms. The invention is not limited to the particular forms disclosed. The invention covers all modifications, equivalents, and alternatives falling within the spirit and scope of the invention as defined by the claims.

Referring now to FIG. 1, an embodiment of an ultrasonic pipe or other structure assessment system constructed in accordance with the present invention is illustrated. The ultrasonic pipe or other structure assessment system is generally designated by the reference numeral 10. The system 10 can be used to identify and evaluate problem areas within a sewer pipe 12. Based on this evaluation recommendations can be made for rehabilitation. The rehabilitation can be conducted to improve structural integrity, restore carrying capacity, and/or reduce operation and maintenance efforts. The goal is to complete the rehabilitation and minimizing surface disruption. It is to be understood that the ultrasonic pipe or other structure assessment system of the present invention can be used to assess other types of pipes than sewer pipes and that sewer pipe 12 is shown for illustration purposes.

The ultrasonic pipe or other structure inspection system 10 of the present invention is particularly useful in that it can operate in sewer lines while they are in operation because they are generally designed to flow seven tenths full. Typical sewer flow rates are two feet per second, which allows some build-up of silt and debris, which then can be discriminated from the pipe or other structure material using this technique. Also, the biological activities of the sludge cause a chemical reaction resulting in a sulfuric acid build-up in the void where it accumulates on the surface and destroys the concrete pipe.

Sanitary Sewer Overflows often pose problems in deteriorating sewer systems. U.S. EPA regulations are expected to have a significant impact on collection system owners and the way in which sewer systems are managed. Properly designed, operated, and maintained sanitary sewer systems are meant to collect and transport all of the sewage that flows into them to a publicly owned treatment works. However, occasional unintentional discharges of raw sewage from municipal sanitary sewers occur in almost every system. These types of discharges are called sanitary sewer overflows. Sanitary sewer overflows have a variety of causes, including but not limited to severe weather, improper system operation and maintenance, and vandalism.

EPA estimates that there are at least 40,000 sanitary sewer overflows each year. The untreated sewage from these overflows can contaminate waters, causing serious water quality problems. It can also back-up into basements, causing property damage and threatening public health.

EPA is proposing to clarify and expand permit requirements for 19,000 municipal sanitary sewer collection systems in order to reduce sanitary sewer overflows. The proposed Sanitary Sewer Overflows Rules will help communities improve some of the Nation's most valuable infrastructure—our wastewater collection systems—by requiring facilities to develop and implement new capacity, management, operations, maintenance and public notification programs.

Deteriorating underground sewer infrastructure is generally not readily identifiable. Failures of sewer lines are often not known until they become an emergency. The ultrasonic pipe or other structure assessment probe system of the present invention shown in FIG. 1 is described in connection with a sanitary sewer. It is to be understood that other types of pipes than sewer pipes can be evaluated using the present invention.

As shown in FIG. 1, a concrete sewer pipe 12 is located in the ground 11. The concrete pipe forms a sewer passage 20. The sewer pipe 12 is partially filled with the fluid 17. A void area 19 is located above the fluid level 18.

The ultrasonic pipe or other structure sewer assessment probe system is generally designated by the reference numeral 13. It includes a central body 14. Three arms 15, 15', and 15" project from central body 14. Three transducers 16, 16', and 16" are located at the ends of arms 15, 15', and 15." The central body 14 contains the electronics and mechanical systems for the ultrasonic sewer assessment probe system 13. The central body 14 is constructed according to known systems for moving through sewers. For example, a robot for the repair of sewer pipes is shown in U.S. Pat. No. 6,101,951 for by Alwin Sigel, patented Aug. 15, 2000. U.S. Pat. No. 6,101,951 states that "The use of robots in the repair of sewer pipes which are not man-sized is already known. Such robots, which are provided with a drive means for moving them through sewer pipes, are suitable, e.g., for the cleaning of sewer pipes, for grinding off irregularities or protrusions or for the mending of leaks. A known multi-segment robot for the above purposes is provided with a rotary head carrying a plurality of treatment tools and a camera. By means of a rotary motor, the rotary head and the robot arm connected thereto can be rotated in a controlled manner by up to 500 degrees about the longitudinal axis. Behind the rotary motor, which is supported on the sewer pipe wall by support wheels, a switch and relay unit is arranged for controlling the functions of the motor. If, for instance, the robot is used to fill leaks or other gaps, a press-out container will be arranged behind the switch and relay unit. The material to be applied is pressed via a hose from the press-out container to the tool arranged on the rotary head and thus can be applied by the tool. Arranged behind the press-out container is a carriage unit for moving the multi-segment robot through the sewer pipe under treatment. For this purpose, the carriage, serving as a tractor, comprises a plurality of wheels driven by a traction motor." The disclosure of U.S. Pat. No. 6,101,951 is incorporated herein by reference.

The ultrasonic inspection system 10 can operate in sewer lines 12 while they are in operation because sewer line 12 is generally designed to flow seven tenths full. Typical sewer flow rates are two feet per second, which allows some build-up of silt and debris, which then can be discriminated from the pipe material using this technique. The ultrasonic inspection system 10 allows the sewer line to remain in operation because the central body 14 and the three arms 15, 15', and 15" that project from central body 14 do not restrict flow of fluid in sewer pipe 19. The central body 14 moves through the sewer pipe 19 and at the same time allow operation of the sewer.

One embodiment of an ultrasonic sewer pipe or other structure assessment probe system of the present invention can be used to provide examination of a sewer system to locate and quantify infiltration and inflow sources. Infiltration is the addition of groundwater to a sewer system at cracks, bad joints, and other imperfections. Inflow is the addition of water to a sewer system from sources including service connections, roof leaders, cellar, yard and area drains, manhole covers, cross connections with the storm sewer and surface run-off. The problems that exist with sewer systems are well known. For example, U.S. Pat. No. 5,150,989 states: "It is generally well known that conduits or pipes which are employed for conducting fluids, for example, sanitary sewer pipes, storm sewer pipes, water lines and gas lines, frequently require repair due to leakage. The leakage may be inwardly, from the environment into the pipe, or outwardly, from the pipe into the environment. Leakage of this type may be due to improper initial installation of the pipe, deterioration of the pipe itself due to aging or the effects of corrosive materials, cracking of the pipe or pipe joints due to environmental conditions such as earthquakes or similar natural or man-made vibrations, or any other such causes. Regardless of the cause, such leakage is undesirable, at best, and may result in waste of the fluid being carried by the pipe, damage to the environment and the possible creation of public health hazards. Because of ever increasing labor and machinery costs, it is becoming increasingly more difficult, at least economically, to dig up and replace those pipes or portions of pipes, which may be leaking. As a result, various methods have been devised for the in situ repair or rehabilitation of the existing pipes, thereby avoiding the expenses and hazards involved in digging up and replacing the pipes." The disclosure of U.S. Pat. No. 5,150,989 is incorporated herein by reference.

A system for assessing pipe or other structure is provided by positioning an ultrasonic transducer proximate the pipe or other structure, producing a fluid connection between the ultrasonic transducer and the pipe or other structure, and moving the ultrasonic transducer relative to the pipe or other structure. The system includes an ultrasonic transducer. The ultrasonic transducer is moved proximate the pipe or other structure. The ultrasonic transducer is carried by a sensor arm. A system is provided for producing a fluid connection between the ultrasonic transducer and the pipe or other structure. The system includes a host pipe. The host pipe produces a column of fluid between the ultrasonic transducer and the pipe. The sensor arm is located inside the host pipe.

Another embodiment of an ultrasonic sewer pipe or other structure assessment probe system of the present invention can be used to identify excessive infiltration and inflow sources. Another embodiment of an ultrasonic sewer pipe or other structure assessment probe system of the present invention can be used to evaluate overall system condition.

It is understood that other types of pipes can also be evaluated using the system of the present invention. The ultrasonic sewer pipe or other structure assessment probe shown in FIG. 1 is only one example of an embodiment of the present invention. Other embodiments of the present invention may include optimization of the number of transducer arms, the ability to adjust to changing pipe diameters, and rotational capabilities to spiral down a pipe, as well as other aspects.

Figure 2:
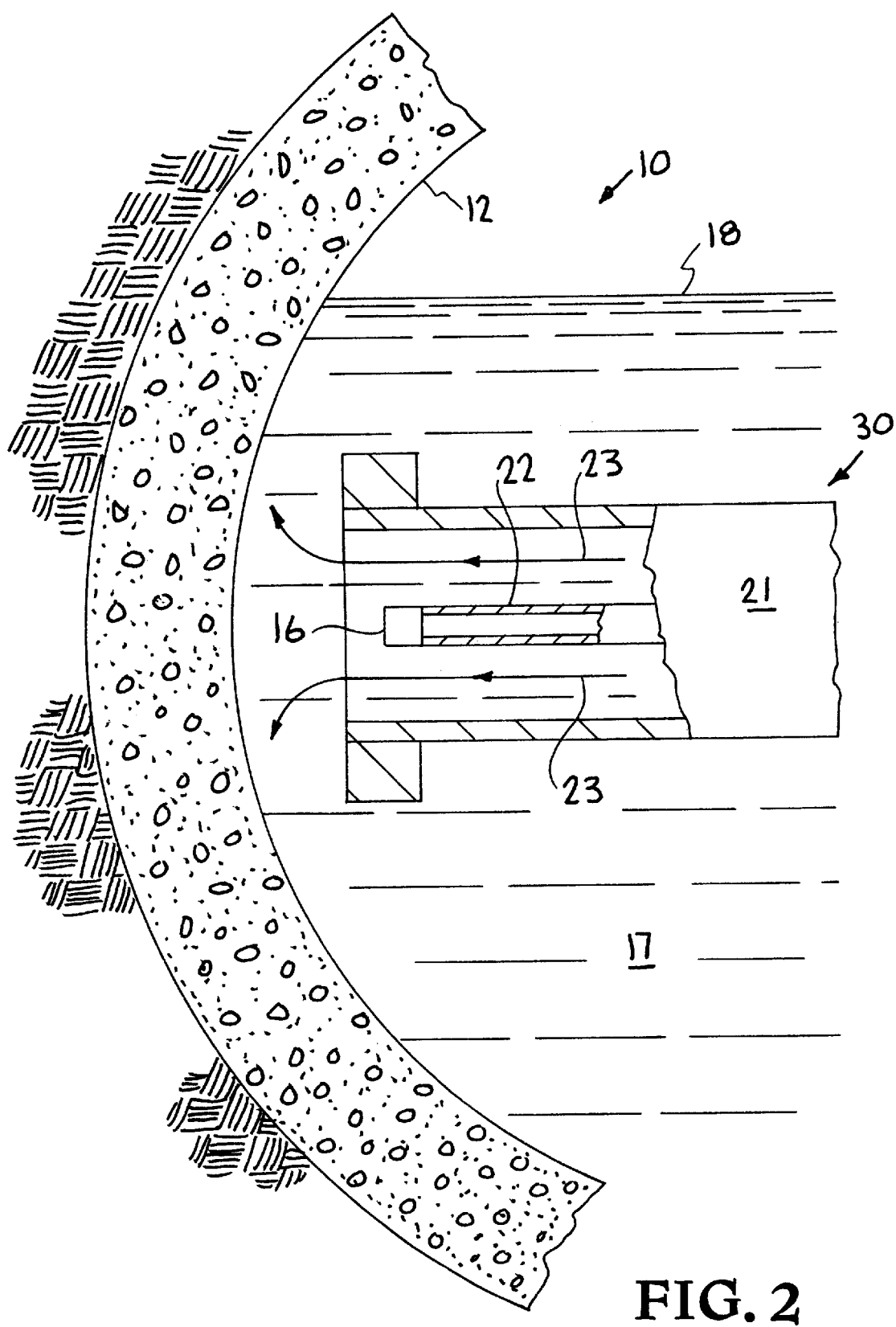
FIG. 2 illustrates additional details of the pipe or other structure assessment probe system shown in FIG. 1.

Referring now to FIG. 2, additional details of the ultrasonic sewer pipe or other structure assessment probe system 13 constructed in accordance with the present invention are illustrated. The system utilizes a "squirter" or "bubbler" approach. This allows the ultrasonic transducers to come into hydraulically direct contact with the pipe walls. This has many advantages and allows the thickness to be measured accurately. An accurate remote assessment can be made in this manner while maintaining continuous operations.

The ultrasonic pipe or other structure sewer assessment probe system is generally designated by the reference numeral 13. The transducer 16 is located at the end of the arm 15. The transducer 16 is carried by a sensor arm 22. The sensor arm is located in a host pipe 21. Water flows through host pipe 21 as shown by the arrow 23 showing the direction of water flow.

Figure 3:
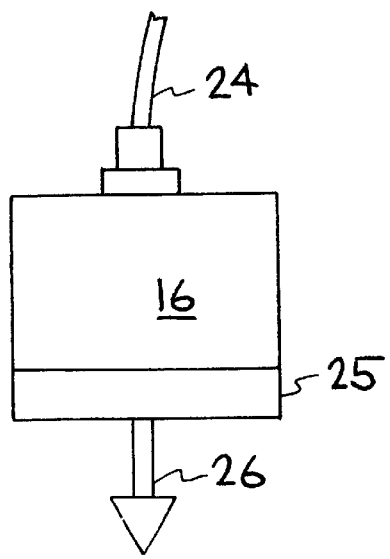
FIG. 3 illustrates additional details of the pipe or other structure assessment probe system shown in FIG. 1.

Additional details of the transducer 16 are shown in FIG. 3. A sonar (ULTRASONIC) transducer provides the appropriate frequency acoustic energy 26 to evaluate the pipe wall 20. The transducer 16 has the necessary power to penetrate the inner pipe wall and reflect off the outside wall. The transducer 16 has a piezoelectric element 25 that converts electrical energy into high frequency mechanical vibrations. This mechanical energy 26 is directed out of the transducer 16 toward the pipe 12. The piezoelectric element 25 also converts mechanical energy 26 into electrical energy. Thus the ultrasonic energy reflected from the pipe 12 will be converted into an electrical signal by the transducer 16. This electrical signal contains information about the condition of the pipe 12.

The electrical pulser/receiver instrumentation in central body 14 generates the electrical signal that excites the transducer 16 and receives the electrical signal from the transducer 16. The electrical connection 24 extends between the transducer 16 and the central body 14. The instrumentation filters the noise, amplifies the signal, and displays the signal for data interpretation. The instrumentation interfaces to a computer for signal processing and analysis. Results of the inspection, such as images of the internal structure of the pipe wall are generated with appropriate software.

Various ultrasonic, transducer and electronics systems can be used in the system shown in FIGS. 2 and 3. For example, an EMAT inspection of header tube stubs developed by McDermott Technology, Inc. and The Babcock & Wilcox Company is shown and described in U.S. Pat. No. 6,079,273, patented Jun. 27, 2000. The disclosure of this patent is incorporated herein by reference.

A hydrogen damage confirmation with EMATs was developed by The Babcock & Wilcox Company and is shown and described U.S. Pat. No. 5,359,898, patented Nov. 1, 1994. The system includes a pair of electromagnetic acoustic transducer coils, which are mounted for movement toward and away from each other. An electromagnet produces pulses that generate acoustic beams across a chord and within the wall thickness of the boiler tube. For adapting to boiler tubes of different outside diameters, the transducer's coils are mounted on a resilient member so that the coils can be pressed against the outer surface of coils having a variety of outside diameters. The angle of the acoustic beam between the coils must also be adjusted, however, and this is done by changing the frequency of energy applied to the coils. The disclosure of this patent is incorporated herein by reference.

A system for inspection of pipes was developed by the Imperial College of Science, Technology of Medicine and is shown and described in U.S. Pat. No. 6,148,672, patented Nov. 21, 2000. The system provides for the propagation of an axi-symmetric Lamb wave of a single mode in one direction along the pipe. A receiver is provided to receive the Lamb wave after its passage along the pipe and convert the received wave for storage, processing and analysis to determine whether or not there are faults present in the pipe. The apparatus includes at least one and usually several excitation rings each having a plurality of Lamb wave exciters deployed in equiangular spacing in a ring clamping structure whereby each exciter can be pressed with equal force against the surface of the pipe under inspection. The disclosure of this patent is incorporated herein by reference.

A system for Lamb wave sonar probe for crack detection and measurement in thin-walled tubing was developed by Combustion Engineering, Inc. and is shown and described in U.S. Pat. No. 5,767,410 patented Jun. 16, 1998. The system provides a probe inspects steam generator tubing for defects. The probe includes a transducer, which generates a localized sonar Lamb wave. The sonar wave is transferred to the tubing by a coupling medium, such as water, that physically couples the transducer and the tubing. Defects in the tubing reflect the sonar wave to the probe, which detects the reflections. The results are then used to determine the length and depth of such defects as cracks, pitting, and thinning. The localized sonar wave performs an inspection sensitive enough to detect ligaments between crack segments. This allows highly accurate predictions of tubing integrity and rupture strength. The disclosure of this patent is incorporated herein by reference.

The ultrasonic sewer pipe assessment probe system of the present invention has the ability to be able to investigate various pipe thicknesses by getting the transducers close to the pipe wall itself. Getting the transducers close to the pipe wall is often made more difficult due to the rough texture of many pipes and the different environments contained within the pipes. The ultrasonic sewer pipe assessment probe system of the present invention manages this problem by fixing the transducer within a host pipe that sends a stream of water around the sensor and to the pipe wall.

The acoustic coupling system (water bubbler) 30 is illustrated in FIG. 2. The water bubbler 30 uses a "squirter" or "bubbler" approach that provides a stream of water from the transducer to the pipe wall. The ultrasonic energy needs a coupling media other than air to propagate. The pipe inspection system of the present invention provides a column of water 23 to transport the acoustic energy 26 from the transducer 16 to the pipe wall 20. The transducer 16 is enclosed in a bubbler device or host pipe 21 that is filled with water and has a hole in the end to allow water to escape. The bubbler 21 is configured so that no air is trapped. A water supply 27 is connected to the bubbler 21 and the flow pressure is adjusted so that the stream of water 23 exiting the bubbler 21 impacts the pipe 12. The acoustic coupling system 30 includes a shoe 29 that encloses the transducer 16, a controllable pump 28, a hose connecting the pump 28 to the shoe 29 and water supply 27.

Using back pressure and temperature gauges, the distance can be quantified and the pipe thickness as well as location of reinforcing can be determined giving a much more accurate reading of the actual pipe condition than is possible using CCTV or Caliper methods. This is a safer and potentially less expensive method that is expected to be far superior to anything currently available.

The direct contact ultrasonic analysis would allow the actual measurement of the pipe thickness and in the case of concrete how much pipe wall was protecting the "re-bar" reinforcing or determine whether the concrete pipe is still there at all! Several other advantages to this approach would include the ability to determine the depth of cracking in the pipe wall and other deformities, as well a: joint integrity with much greater reliability and without the risks of walk through inspections.

This ultrasonic device 10 will generate longitudinal and shear energy by adjusting the angle of the transducer head relative to the pipe wall. The longitudinal waves allow wall thickness measurements, circumferential defect detection, and characterizing the condition of the soil outside of the pipe. Shear wave interrogation will detect defects orientated normal to the wall surfaces.

Figure 4:
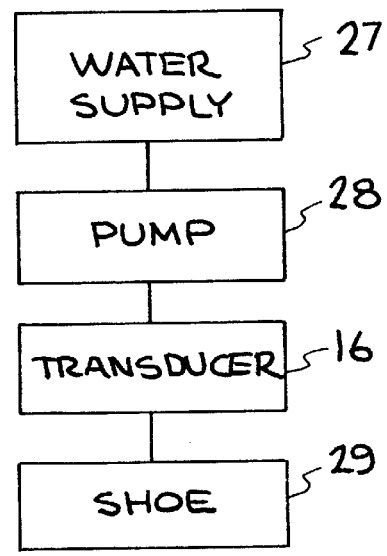
FIG. 4 illustrates additional details of the pipe or other structure assessment probe system shown in FIG. 1.

Another embodiment of the present invention will be described with reference to FIG. 4. In this embodiment a system for assessing various type of pipe or other structures is described wherein an ultrasonic transducer is fluidly connected to the other structure. The "pipe or other structure" may be any type of pipe that needs inspecting or it may be other structures that need inspecting such as a wall, a dam, or a floor that needs inspecting. A fluid connection is made between an ultrasonic transducer, such as transducer 16 shown in FIG. 4, and the pipe or other structure. The ultrasonic transducer is moved proximate the pipe or other structure. Movement of the ultrasonic transducer may be circular, vertical, horizontal, or any other direction, or it may a combination of such movements. The movement can be accomplished by mechanical equipment or by hand. The system includes means for producing a fluid connection between the ultrasonic transducer and the pipe or other structure. This may be a conduit for channeling the fluid proximate the pipe or other structure. The conduit may be a solid pipe or it may be a flexible conduit such as a rubber or plastic hose. The fluid is moved through the conduit by a fluid movement means such as a pump, for example pump 28 shown in FIG. 4, or by natural means such as gravity. The fluid movement means produces a column of fluid between the ultrasonic transducer and the pipe or other structure. Instead of a shoe 28 as shown in FIG. 4, the conduit can directly connect the fluid to the pipe or other structure.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

What is claimed is:

1. An apparatus for assessing a sewer pipe that is generally horizontal and can be up to seven tenths filled with a flowing fluid, said sewer pipe having a diameter and a sewer pipe wall comprising:
    a central body having a body diameter sufficiently smaller than said diameter of said sewer pipe to allow said flowing fluid to pass said central body, at least three arms projecting radially outward from said central body, each of said arms having an inner end connected to said central body and an outer end remote from said central body,
    at least three ultrasonic transducers an ultrasonic transducer attached to each said outer end of said at least three arms,
    said arms being positioned relative to said central body and said sewer pipe so that each said ultrasonic transducer is positioned proximate said sewer pipe wall and said flowing fluid can pass said central body, can pass said at least three arms, and can pass said at least three ultrasonic transducers, and
    a system for producing a water connection between each said ultrasonic transducer and said sewer pipe wall by providing water through each said at least three arms and between each said ultrasonic transducer and said sewer pipe wall.

2. The apparatus for assessing a sewer pipe of claim 1 wherein said system for producing a water connection between said ultrasonic transducer and said sewer pipe wall produces a column of water between said ultrasonic transducer and said sewer pipe wall.

3. The apparatus for assessing a sewer pipe of claim 2 wherein said column of water between said ultrasonic transducer and said sewer pipe wall is carried by a host pipe.

4. The apparatus for assessing a sewer pipe of claim 3 wherein said host pipe directs said column of water proximate said ultrasonic transducer and proximate to said sewer pipe wall.

5. The apparatus for assessing a sewer pipe of claim 4 wherein said ultrasonic transducer comprises a piezoelectric element that converts electrical energy into high frequency mechanical vibrations.

6. The apparatus for assessing a sewer pipe of claim 5 wherein said piezoelectric element is located inside said host pipe.

7. The apparatus for assessing a sewer pipe of claim 6 wherein said piezoelectric element only partially fills said host pipe.

8. The apparatus for assessing a sewer pipe of claim 7 wherein said a fluid has a fluid flow and said central body allows said fluid flow.

9. The apparatus for assessing a sewer pipe of claim 1 wherein said ultrasonic transducer is a Lamb wave sonar transducer.

10. The apparatus for assessing a sewer pipe of claim 1 wherein said ultrasonic transducer produces longitudinal waves.

11. The apparatus for assessing a sewer pipe of claim 1 wherein said ultrasonic transducer produces shear waves.

12. The apparatus for assessing a sewer pipe of claim 1 wherein said ultrasonic transducer produces longitudinal waves and shear waves.

13. An apparatus for assessing a sewer pipe that is generally horizontal and can be up to seven tenths filled with a flowing fluid, said sewer pipe having a diameter and a sewer pipe wall comprising:
    a central body having a body diameter sufficiently smaller than said diameter of said sewer pipe to allow said fluid to pass said central body,
    at least three arms projecting radially outward from said central body, each of said arms having an inner end connected to said central body and an outer end remote from said central body,
    at least three ultrasonic transducer means for sending and receiving ultrasonic signals, each ultrasonic transducer means attached to each said outer end of said at least three said arms,
    said arms being positioned relative to said central body and said sewer pipe so that each said ultrasonic transducer means is positioned proximate said sewer pipe wall and said flowing fluid can pass said central body, can pass said at least three arms, and can pass said at least three ultrasonic transducer means, and
    means for producing a water connection between each said transducer means and said sewer pipe wall by providing water through each said at least three arms and between each said ultrasonic transducer means and said sewer pipe wall.

14. The apparatus for assessing a sewer pipe of claim 13 wherein said means for producing a fluid connection between said transducer means and said pipe includes means for producing a column of said water between said transducer means and said sewer pipe wall.

* * * * *